United States Patent [19]
Haring et al.

[11] Patent Number: 5,218,416
[45] Date of Patent: Jun. 8, 1993

[54] IRRADIANCE CALIBRATION WITH SOLAR DIFFUSER

[75] Inventors: Robert E. Haring, Alta Loma; Herbert A. Roeder, Brea; Ulli G. Hartmann, Huntington Beach, all of Calif.

[73] Assignee: The Perkin-Elmer Corporation, Norwalk, Conn.

[21] Appl. No.: 810,792

[22] Filed: Dec. 19, 1991

[51] Int. Cl.$^5$ ............................................. G01N 21/33
[52] U.S. Cl. ................................. 356/243; 250/372; 250/252.1
[58] Field of Search ............... 356/243; 250/252.1 A, 250/372

[56] References Cited

U.S. PATENT DOCUMENTS 4,652,761  3/1987  Kerr et al. ........................... 250/372

*Primary Examiner*—Vincent P. McGraw
*Attorney, Agent, or Firm*—Edwin T. Grimes; Joseph R. Dwyer

[57] ABSTRACT

The sun's energy is used in combination of movable and fixed diffuser plates, windows and apertures which are positioned in a series of test sequences (modes) for reflectance monitoring and calibration without the use of man-made sources. There are three embodiments, or implementations, of the invention—one embodiment uses two diffusers—a working diffuser and a secondary diffuser—the second embodiment uses three diffusers, a working diffuser, a secondary diffuser and a reference diffuser—and the third embodiment uses two diffusers—a working diffuser and a secondary diffuser, the latter also functioning as a cover for the working diffuser. The movable diffusers are mounted on rotatable cones and, in all embodiments, the sun is blocked from reaching the diffusers when not in use. Thus, the sun is used as a stable source for calibration and monitoring and the sun/diffuser combination is used in such a way that the response of all elements of the optical subsystem of the TOMS can be unambiguously and efficiently characterized with high accuracy and precision.

14 Claims, 9 Drawing Sheets $\theta = \cos^{-1}(R/(R+H))$

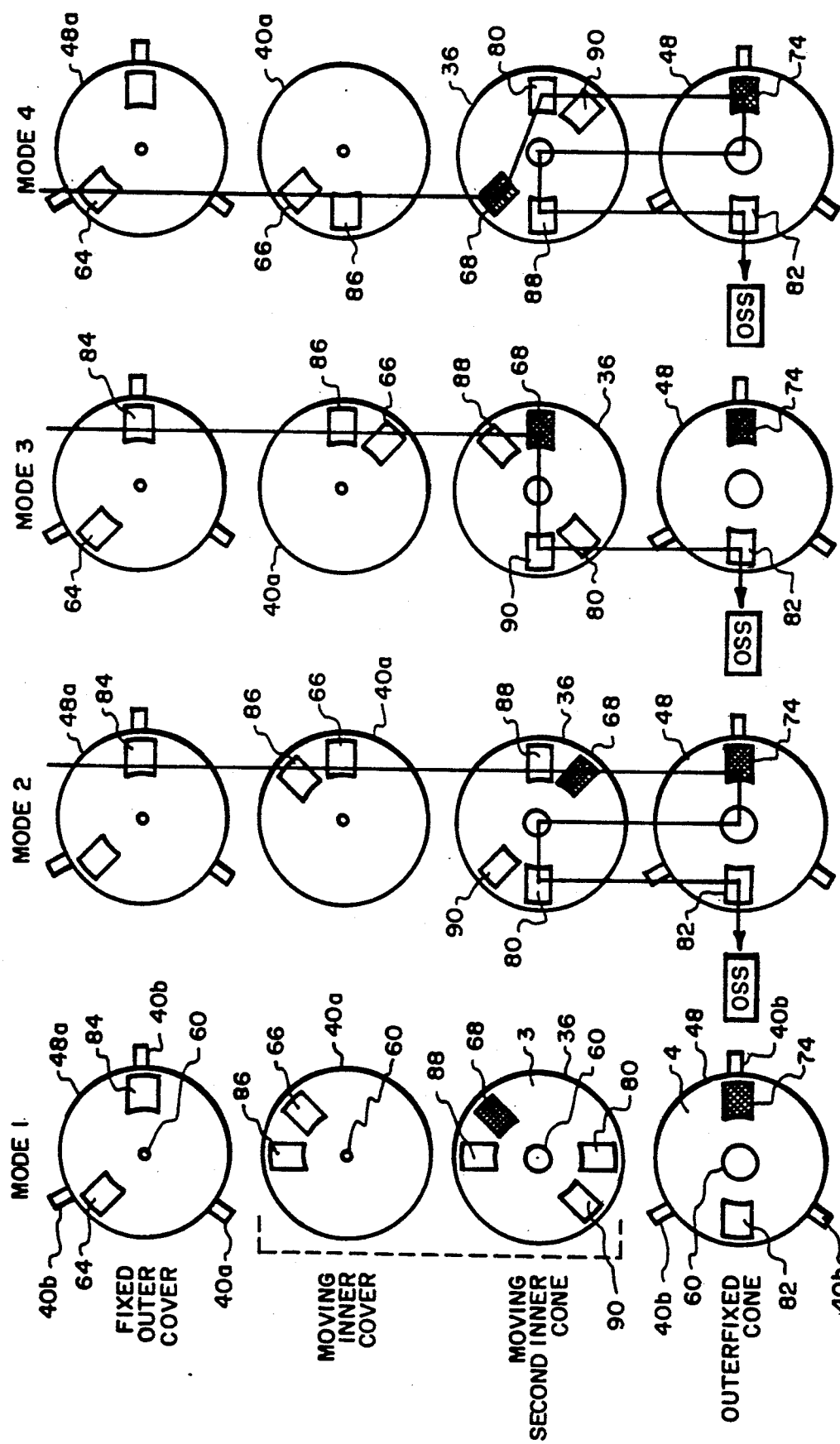

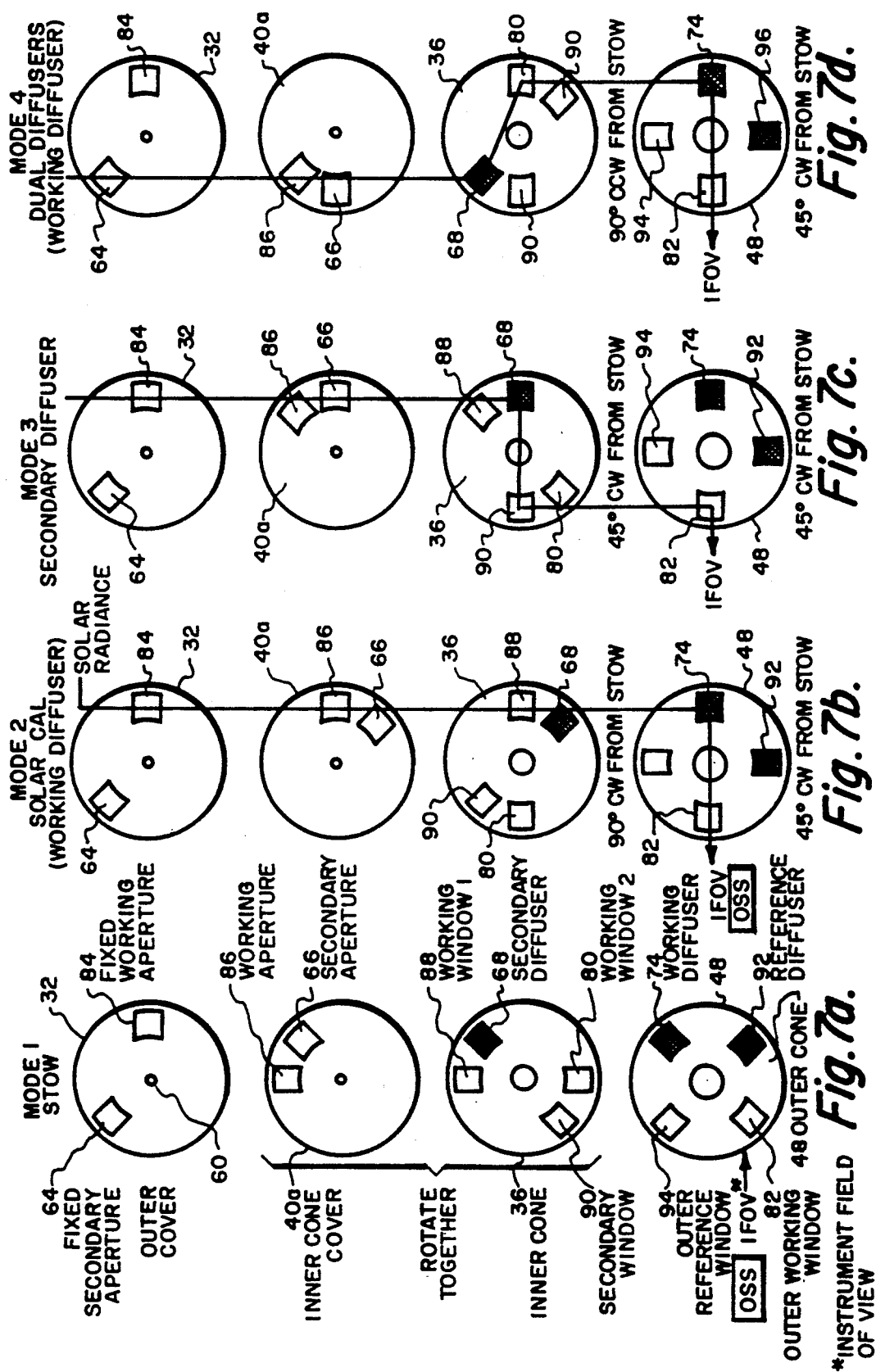

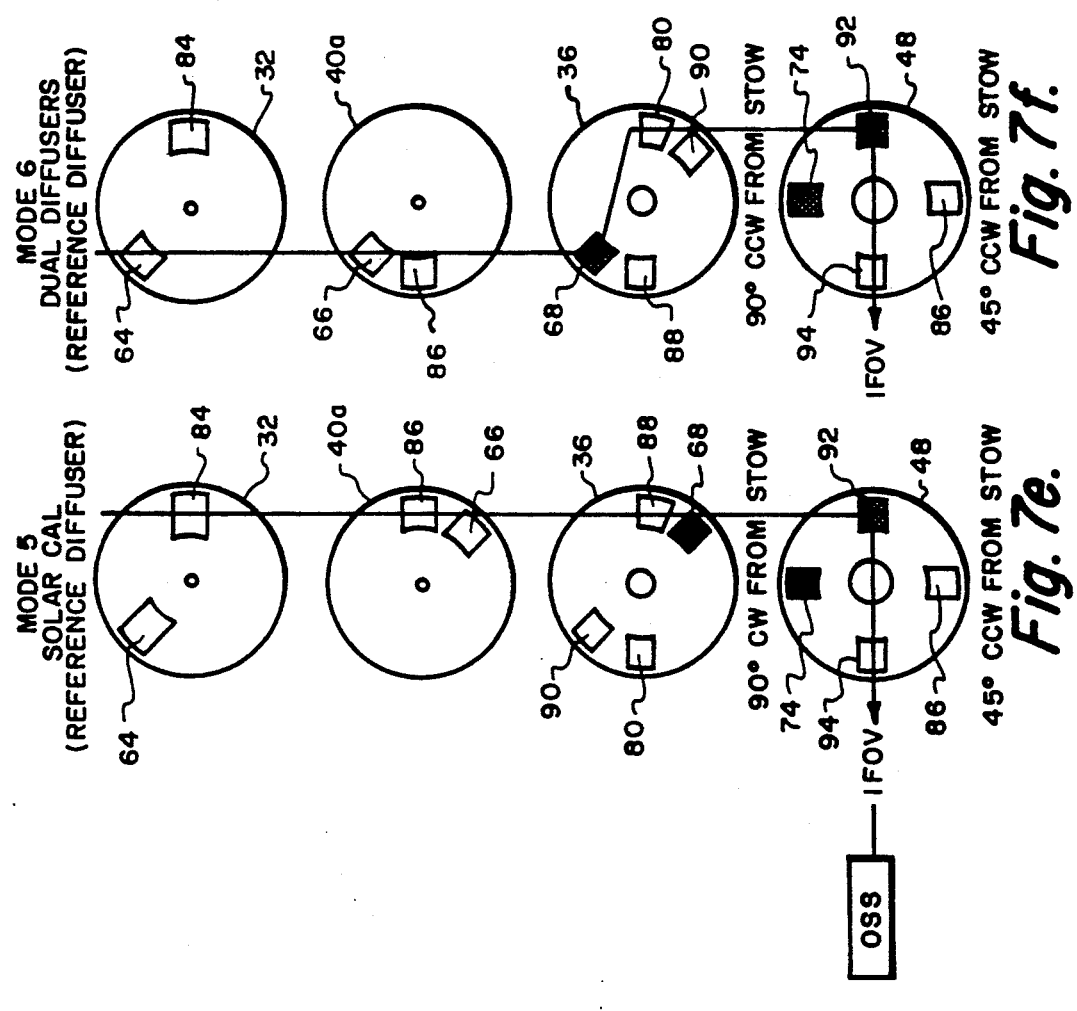

MODE 1 — STOW

MODE 2 — DIFFUSER (SOLAR CALIBRATION)

MODE 3* — DIFFUSER IRRADIATED BY DIFFUSER

MODE 4* — DIFFUSER

*REFLECTANCE MONITORING MODES

IRRADIANCE CALIBRATION WITH SOLAR DIFFUSER

GOVERNMENT RIGHTS

The invention described herein was made in the performance of work under NASA Contract No. NAS5-30517 and is subject to the provisions of Section 305 of the National Aeronautics and Space Act of 1958 (42 U.S.C. 2457).

BACKGROUND OF THE INVENTION

This invention relates, in general, to a means of calibrating a space borne spectrometer and thus improve the operation of the Total Ozone Mapping Spectrometer (TOMS) for measuring stratospheric ozone variations from a satellite.

This improvement removes the effects of spectral changes and stability variations in the calibration source (heretofore man-made) and in the diffuser plate required in the TOMS.

The TOMS basically measures changes in signal levels which are changes in the amount of radiation entering the TOMS and consists of two main subsystems, optics and electronics. As radiation enters the TOMS, the energy passes through the optical subsystem before being processed as an electronic signal in the electronic subsystem. The electronic subsystem can be readily calibrated in space, however, the optical subsystem is not readily characterized and obviously both must be calibrated for the TOMS to provide valid ozone data.

Also, the optical subsystem components in the TOMS are subject to degradation due to contamination and aging. There is no direct way of establishing the amount of degradation. This is usually measured by directing the energy of a known source (man-made) through the optical subsystem and measuring the electronic subsystem response. Theoretically, the TOMS has on-board calibration features which establish the optical subsystem response to known stimuli (source), and in this way, changes in the electronic and optical subsystem response can be segregated. In practice, however, one difficulty is in finding a source which can reliably perform those measurements for years in space without itself degrading and failing. Man-made sources, such as mercury, hydrogen and tungsten lamps, which heretofore have been used to calibrate optical subsystems in the ultraviolet wavelength region, have limited life and are subject to failure. In addition, these man-made sources consume power.

In the past, the sun's energy has been used to calibrate the TOMS with the required diffuser plate directing the energy into the optical subsystem and subsequently into the electronic subsystem, but any change in diffuser plate reflectance was indistinguishable from optical and electronic substances response changes.

Therefore, it is an object of this invention to provide the TOMS with a Solar Reflectance Calibration Assembly (SRCA) which will enable the optical subsystem of the TOMS to be monitored and calibrated over a long time period.

SUMMARY OF THE INVENTION

The present invention which meets the foregoing object utilizes the sun's energy with a unique combination of movable and fixed diffuser plates, windows and apertures which are positioned in a series of test sequences (modes) for reflectance monitoring and calibration without the use of man-made sources.

There are three embodiments, or implementations, of the invention—one embodiment uses two diffusers—a working diffuser and a secondary diffuser—the second embodiment uses three diffusers, a working diffuser, a secondary diffuser and a reference diffuser—and the third embodiment uses two diffusers—a working diffuser and a secondary diffuser, the latter also functioning as a cover for the working diffuser. The movable diffusers are mounted on rotatable cones and, in all embodiments, the sun is blocked from reaching the diffusers when not in use.

Thus, the sun is used as a stable source for calibration and monitoring and the sun/diffuser combination is used in such a way that the response of all elements of the optical subsystem of the TOMS can be unambiguously and efficiently characterized with high accuracy and precision.

DETAILED DESCRIPTION

Figure 1:
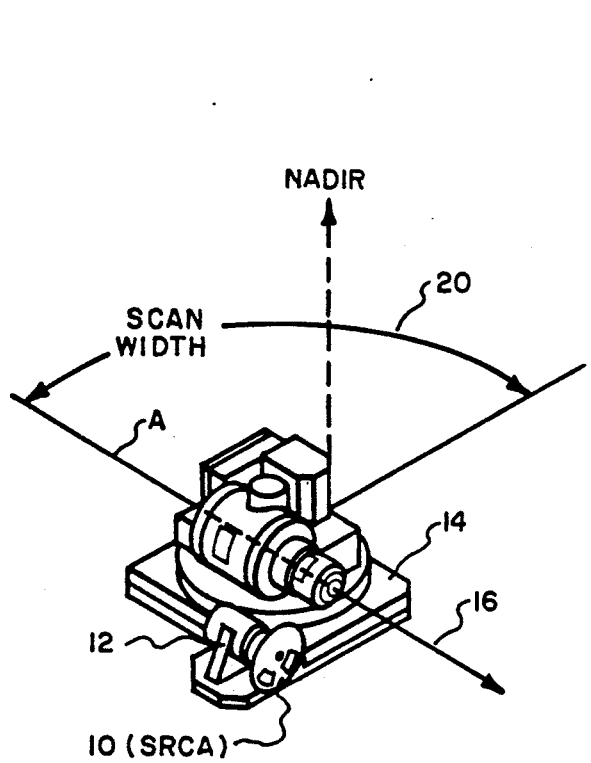
FIG. 1 is a perspective view of the TOMS and the SRCA and their orientation with respect to the spacecraft orbit and the sun.

FIG. 1 shows the SRCA on a mounting bracket 12 attached to the TOMS 14. This Fig. also shows the spacecraft velocity vector 16 and scan width 20.

Figure 1A:
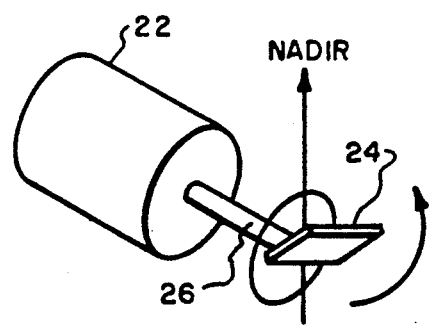
FIG. 1a is an enlargement of the scan motor and mirror of FIG. 1 with the instrument mirror oriented toward NADIR for ozone mapping.
Figure 1B:
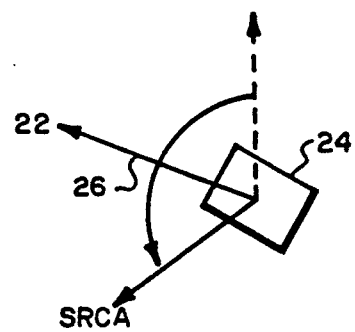
FIG. 1b shows the scan motor and mirror of FIG. 1a rotated to direct solar flux to the SRCA for solar calibration.

FIG. 1a shows a scan motor 22 with a mirror 24 of the SRCA of FIG. 1 mounted on a hollow shaft 26. Mirror 24 is normally oriented within the scan width in the ozone mapping mode as in FIG. 1a so that the solar irradiance will be directed through the hollow shaft 26 into the TOMS and as shown in FIG. 1b is then rotated 90° to direct the reflected solar irradiance toward the SRCA for the SRCA mode.

Figure 2:
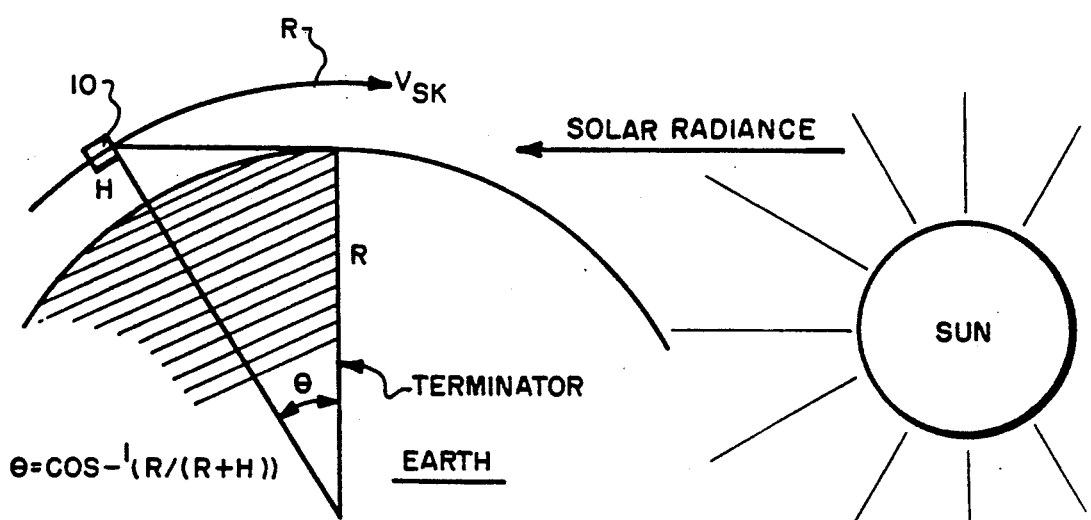
FIG. 2 shows the solar calibration geometry with respect to the earth and sun.

FIG. 2 shows the solar calibration geometry where only a short portion of the orbit time is used (about 8 minutes). Day-night terminator, shown as radius R, defines the shadowing from the sun and as the TOMS approaches the terminator, it first sees the sun at point H where the sun is now incident on the diffusers to use the SRCA for solar calibration. After point R, the TOMS returns to its normal scan mode for mapping ozone.

The data required for normal solar calibration can be obtained in less than 5 seconds. For the diffuser reflectance measurement, data is obtained over multiple orbits and integrated to obtain the required accuracy.

Figure 3A:
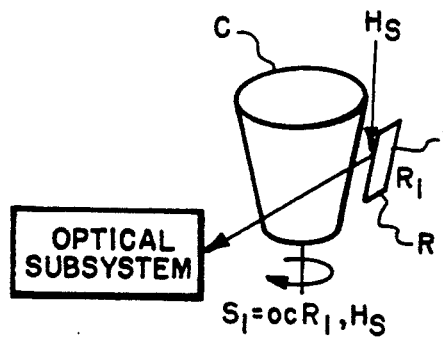
FIGS. 3a-3c are simplified schematic illustrations of the diffuser reflectance analysis utilizing a working diffuser and a secondary diffuser.
Figure 3B:
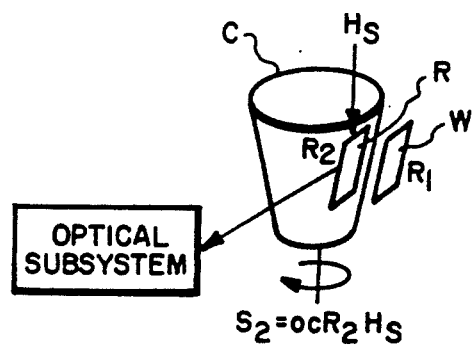
Figure 3C:
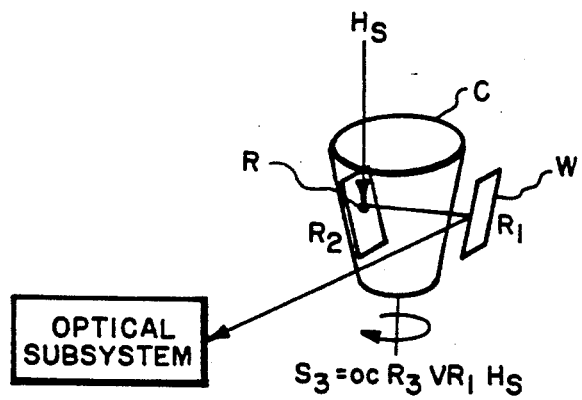

FIGS. 3a-3c illustrate schematically the diffuser reflectance monitoring analysis. Solar radiance uniformly illuminates all of the diffusers, uses no power, is temporally and spectrally stable and is constantly monitored to a high degree of accuracy by other instruments. The method for monitoring the reflectance of both a working diffuser W with reflectance $R_1$ and a secondary diffuser S with reflectance $R_2$ located relative to a cone C, all representative of the SRCA of this invention.

FIG. 3a (Mode 1) shows the working diffuser W in its normal operating mode. The solar irradiance $H_s$ impinges upon the working diffuser R which directs the reflected solar irradiance toward a scan mirror (not shown) in the optic subsystem. The signal output $S_1$ is proportional to the reflectance $R_1$ of the diffuser W, the solar irradiance $H_S$ and a geometry factor. In FIG. 3b (Mode 2), the secondary diffuser S with exactly the same geometry as the diffuser W is rotated about the axis of a cone such that the solar irradiance is reflected from it into the scan mirror. While in this position, the secondary diffuser S blocks off the working diffuser W. The signal received, $S_2$, is now proportional to the reflectance $R_2$ of the secondary diffuser S. FIG. 3c (Mode 3) shows a third mode where the secondary diffuser S is located on the opposite side of the cone C but at the same solar incidence angle as in the other modes. The reflected solar irradiance of the secondary diffuser S now illuminates the working diffuser W. Resulting signal $S_3$ is therefore proportional to the product of the two reflectances, the same angular geometry factor and a visibility factor V. This visibility factor represents the percentage of energy seen by the working diffuser as it views the secondary diffuser. It is comprised of a view factor and, if angles change, a bi-directional reflectance factor.

In the following paragraphs concerning diffuser measurements, signal-to-noise ratio, etc., reference to the SRCA of FIGS. 3a-3c is made. The secondary diffuser can be considered a reference diffuser in FIGS. 3a-3c and will be referred to as such in the following paragraphs.

The fraction of radiant energy transferred from the reference diffuser S to the working diffuser W during Mode 3 operation affects the signal level and therefore the precision to which the Mode 3 measurements are made. Averaging many measurements improves the precision but there are practical limits since the sun is within the SRCA's field of view for only a fraction of the orbit period and data for Modes 2 and 3 would normally be taken together within this time frame. A practical lower limit for the radiant energy transfer required from reference diffuser S to working diffuser W is 4%.

The efficiency of radiant energy transfer between the reference and working diffusers S and W, can be estimated for various geometries by assuming the diffusers are lambertian and calculating their geometrical configuration factor or view factor. Solutions for many common geometries have been tabulated in reference books on radiative heat transfer. The techniques of configuration algebra allow broader application of the general solutions. A solution for the general geometry involved in the SRCA was found and used to estimate possible efficiencies for radiant transfer between the devices in mode 3 operation. The upper limit for the fraction of reflected solar irradiance listed for the solar diffuser, 8%, is based on diffusers of equal size with one edge in contact. An accurate prediction of the performance of the SRCA can be obtained by numerical integration of the measured bi-directional reflectance function of the diffusers. NBS monograph 160, "Geometrical Consideration and Nomenclature for Reflectance" presents applicable nomenclature for characterizing the bi-directional reflectance function.

The two diffusers S and W can be considered Lambertian, both singly and in combination, to permit absolute determination of reflectance. For:

$K$ = instrument response in counts/Watt onto the detector

= (detector response in $A/W$) × (electronics response in counts/$A$)

$T$ = instrument throughput, fraction of photons into the entrance aperture reaching the detector where both K and T are assumed a slowly varying function of time that is essentially constant during any particular calibration measurement. Then the radiance illuminating the instrument field of view is:

Radiance = $a \times R_n \times H$ and the instrument signal response in counts is:

$S_1 = a \times H \times R_1 \times T \times K$ $S_2 = a \times H \times R_2 \times T \times K$ where $R_n$ is the reflectance of diffuser n, a is the angular factor relating radiance to irradiance for a Lambertian surface, and H is the solar irradiance. A third measurement uses the radiance of the working diffuser W to illuminate the reference diffuser S. The instrument signal response in counts in this case is:

$S_3 = ((a \times H \times R_1) \times V) \times R_2 \times T \times K$ where V is a mechanical view factor, or visability factor, of the reference diffuser S illuminated by the working diffuser W. This view factor is determined by geometry only, does not change, and can be precisely measured on the ground. From the ratios of the three measurements:

$S_3/S_1 = V \times R_2$ $S_3/S_2 = V \times R_1$ $R_1$ and $R_2$ are determined directly since V is known. With diffuser reflectance R measured, $T \times K$ can be calculated since $a \times H$ is known and therefore the desired instrument calibration has been fixed. This concept requires three sets of measurements to establish reflectance values, one from each of the two diffusers S and W individually, and one from the two diffusers S and W in "series".

FIRST EMBODIMENT

Figure 4:
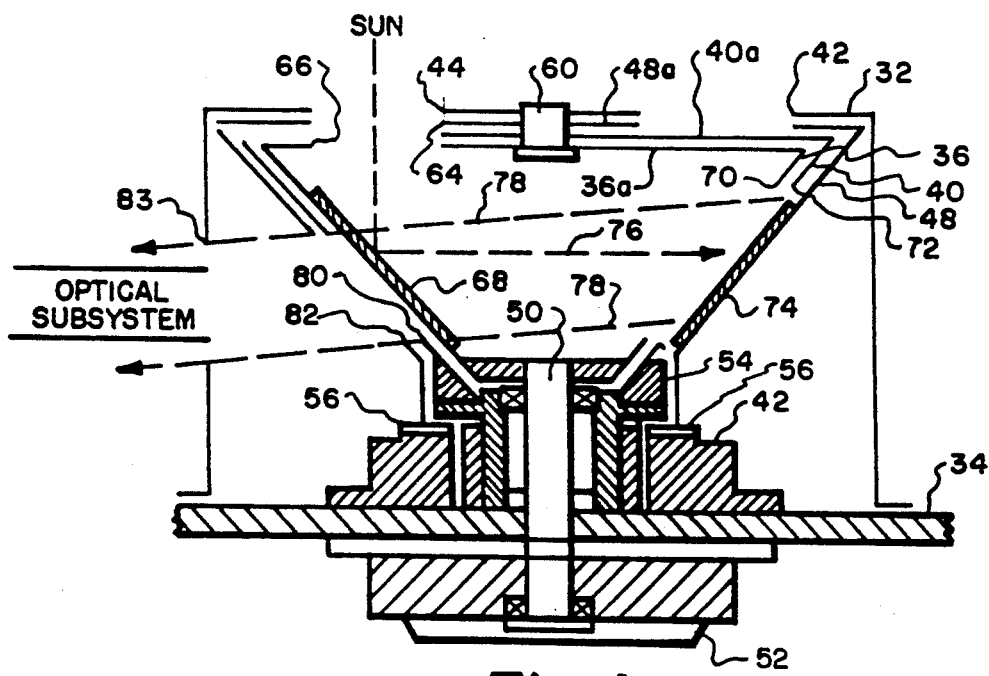
FIG. 4 is a cross-sectional view of the first embodiment of the SRCA.
Figure 5A:
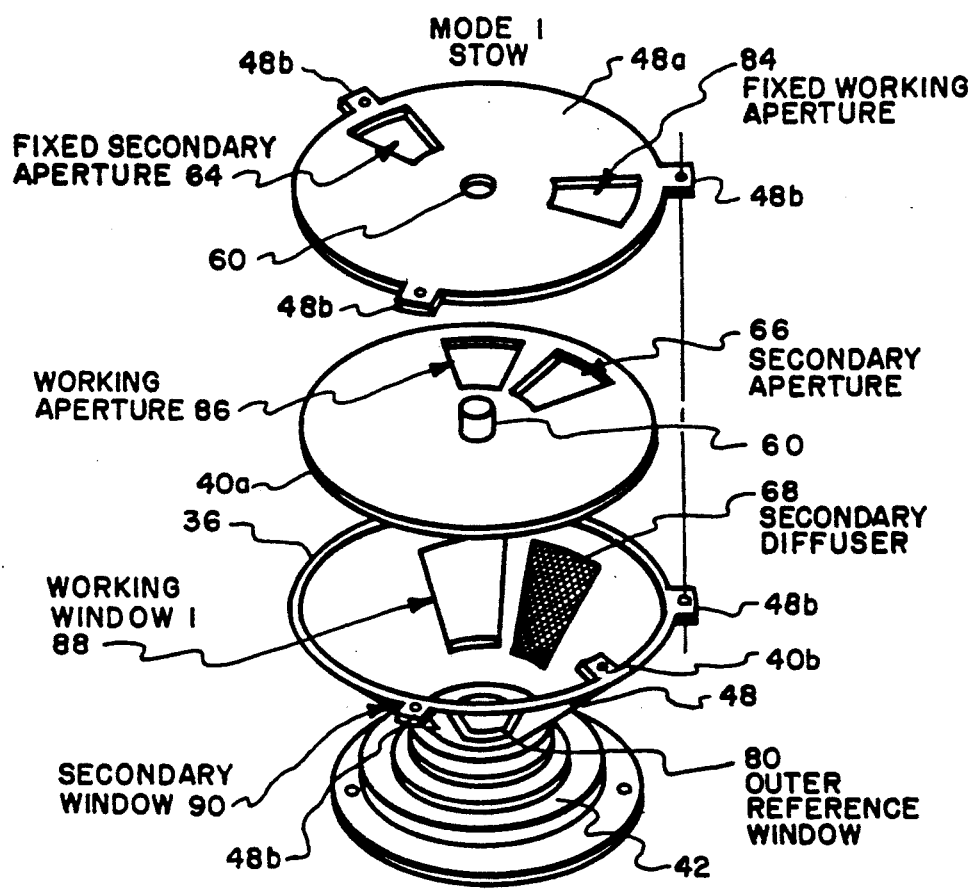
FIGS. 5a and 5b are exploded view of the SRCA to more clearly show the locations of the diffusers, windows and apertures and the modes used in its calibration, FIGS. 5c-5f schematically illustrate the calibration modes for the solar calibration of the SRCA of FIGS. 4, 5a and 5b.
Figure 5B:
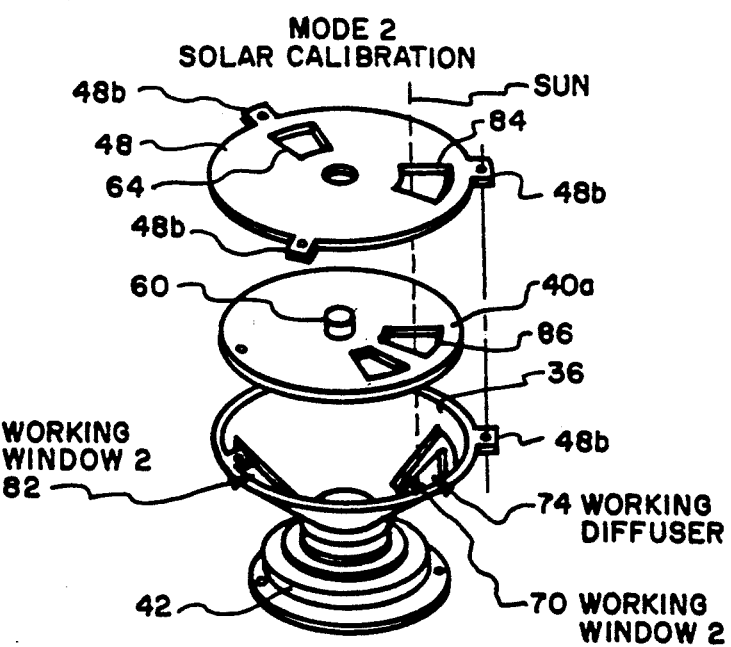

At the outset it should be noted that FIGS. 4 and FIGS. 5a and 5b are schematized essentially to show the path of the diffused solar flux within the SRCA and the location of the diffusers within an actual embodiment of the invention. Therefore, some of the apertures and windows in FIG. 4 are not necessarily oriented as in FIGS. 5c-f are the top cover of one cone is shown in FIGS. 5a and 5b although they are not connected together.

However, FIG. 4 together with the exploded views in FIGS. 5a and 5b do show the first embodiment of the SRCA as having a diffuser housing, which comprises a stationary outer cover 32 attached to a base 34, and two cones, a first inner cone 36 and a second inner cone 40, both of which are rotatable by a tandem motor 42. The top of the outer cover 32 has an aperture 44 and a aperture 46. Also shown is a fixed outer cone 48. The outer cover 32 and base, however, are not shown in FIGS. 5a and 5b, for clarity.

As shown in FIG. 4, the first inner cone 36 has an integral top cover 36a and the second inner cone 40 has a top cover 40a as will be apparent in FIGS. 5c-4f. The first inner cone 36 is rotated by shaft 50 within the second inner cone 40 and a position encoder 52 verifies the position of the first inner cone 36. The second inner cone 40 is mounted on a fixture 54 for rotation and a second encoder 56 verifies the position of cone 40. The outer fixed cone 48 has a top cover 48a attached thereto by suitable means 48b, shown as tabs and bolts represented by dashed lines. Not shown are the attaching means for the other top covers but they are essentially the same as attaching means 48b. All cones have a cone support pivot 60 located centrally of the outer cover 32 and top cover 36a, 40a, and 48a for stability.

FIG. 4 also shows the solar irradiance entering the SRCA through aperture 44 in cover 32 and through a fixed secondary aperture 64 in top cover 40a and through a secondary aperture 66 in top cover 36a where the solar flux is diffused by a secondary diffuser 68 (S in FIGS. 3a-3c) and directed through aperture 70 in the first inner cone 36 and aperture 72 in the second inner cone 40 toward a working diffuser 74 (W in FIGS. 3a-3c) as represented by arrows 76. Working diffuser 74 is located on the fixed outer cone 48a. Arrows 78 show the path of the diffuse reflected light directed through aperture 80 in the second inner cone 36, a working window 82 in the outer cone 48 where the diffused radiation is then directed out a field-of-view aperture 83 located in the side of the cover 32. As mentioned before, the primary purpose of FIG. 4 is to show the path of the solar flux as it is directed out the field-of-view aperture 83.

Referring now to FIG. 5a, this figure shows that a fixed working aperture 84 in the top cover 48a is located about 135° from the fixed secondary aperture 64, that a working aperture 84 is in the top cover 48a and that a working aperture 86 is located about 45° from the secondary aperture 66 in the top cover 40a. In order to more clearly see the first inner cone 36 reference is made to FIGS. 5c-5f. The cone 40 is not shown in FIGS. 5a and 5b nor in FIGS. 5c-4f.

The first inner cone 36 has a first working window 88 located about 45° from the secondary diffuser 68 and in vertical alignment with apertures 64 and 86. The first inner cone 36 also has a secondary window 90 located diametrically opposite the secondary diffuser 68. The outer reference window 80 is diametrically opposite the working window 88. Note that apertures 44 and 46 in the cover 32 both appear in FIG. 4 even though they are at an angle to each other corresponding to the angle between the fixed aperture 64 and fixed working aperture 84.

FIG. 5a (Mode 1) is the stow position for the SRCA. The top cover 48a is positioned such that the space between the fixed secondary aperture 64 and the fixed working aperture 84 covers the working aperture 86 and the secondary aperture 66 in the top cover 40a thus blocking the sun from entering the SRCA.

FIG. 5b (Mode 2) is the solar calibration mode for the SRCA as in FIG. 3a. The second inner cone 40 and its top cover 40a have been rotated about 45° so that the working aperture 86 is immediately beneath the fixed working aperture 84 so that the sun may impinge on the working diffuser 74 which in turn directs diffused light out the second working window 82. This is clearly shown in FIG. 5b.

FIGS. 5c-5f show the modes of calibrating the first embodiment of the SRCA.

In these figures, the cover 32 is not shown and the top cover 48a and the outer fixed cone 48, shown separately, are both fixed against rotation. Also, the second inner cone 40a is shown but its cone 40 is not shown. Again, cone 40 is used to rotate the top cover 40a and will contain apertures and windows where necessary. The moving inner cone 36 is shown without its cover 36a. The omission of the above mentioned components is to enable these figures to show the various calibration steps by the rotation of the two inner cones, the location of the various apertures, window, and diffusers, and to show the direction of the solar flux throughout the figures.

Mode 1 (FIG. 5c) represents the stow position. This corresponds to FIGS. 5a. The moving inner cone cover 40a is located such that the working and secondary apertures 86 and 66 are within the space between the fixed secondary aperture 64 and the fixed working aperture 84 in the outer cover 48a so that the solar flux is blocked from reaching any diffuser or window in the cones.

Mode 2 (FIG. 5d) represents the solar calibration utilizing the working diffuser 74. This is the normal working mode of the SRCA. the moving inner cone 40a has been rotated about 45° clockwise from the stow position (Mode 1) and the moving second inner cone 36 has been rotated about 90° clockwise from the stow position. In this mode, solar flux enters the fixed working aperture 84, through secondary aperture 66, through the inner window 88 and impinges upon the working diffuser 74 which directs its reflected diffused radiation through outer reference window 80 and through window 82.

Mode 3 (FIG. 5e) represents the secondary diffuser calibration. The moving inner cover 40a has been rotated about 45° from Mode 2 position and the moving inner cone 36 has been rotated counter clockwise about 45° from the Mode 2 position. In this Mode, solar flux enters the fixed working window 84 and through the working window 84, impinges upon the secondary diffuser 68 which directs its diffused reflected radiation through outer reference window 90 and through window 82.

Mode 4 (FIG. 5f) represents the calibration of the working diffuser and in this Mode, the moving inner cover 40a has been rotated 180° clockwise, or counter clockwise from Mode 2 position, and the moving second inner cone 36 has been rotated 135° counter clockwise from Mode 3 position so that solar flux may enter through the secondary aperture 66 and impinge upon the secondary diffuser 68. Reflected diffused solar flux from diffuser 68 enters the outer reference window 80 and impinges upon the working diffuser 74 which directs its diffused reflected radiance out working window 88 and through window 82.

SECOND EMBODIMENT

In this embodiment, those elements having the same function as in the previous embodiment will be given the same reference numerals for simplicity of description.

Figure 6:
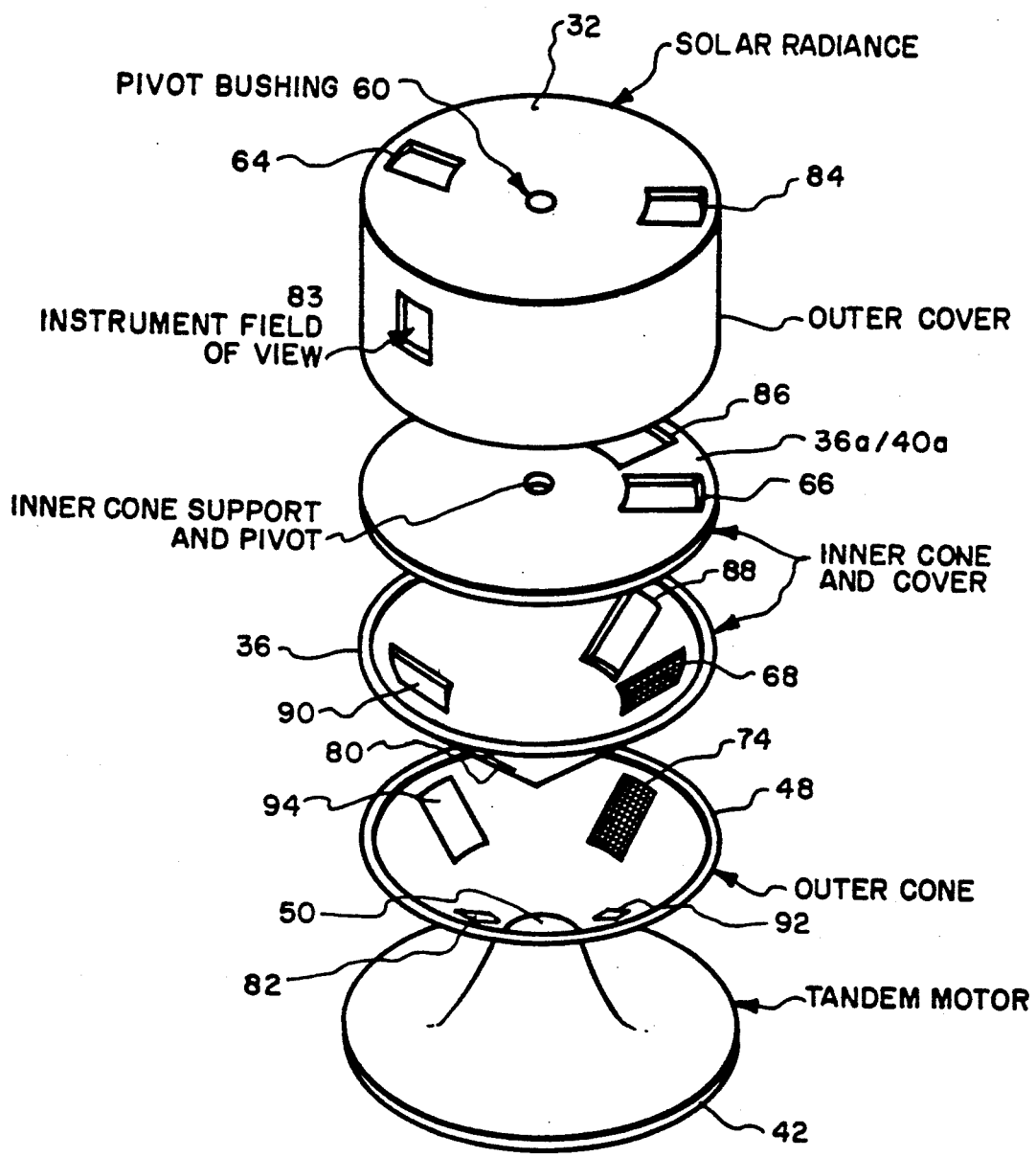
FIG. 6 is an exploded view of the second embodiment of the SRCA showing the locations of the diffusers (including an additional reference diffuser), windows and apertures, FIGS. 7a-7f schematically illustrate the modes used in solar calibration of the SRCA of FIG. 6.

Taking FIGS. 6 and 7a together, it can be more clearly seen that fixed secondary aperture 64 and the fixed working aperture 84 are located in the top of the cover 32 and the field-of-view aperture 83 is located on the side of the cover 32. Apertures 64 and 84 are located about 135° apart. The cover 32 is essentially the same as in FIG. 4. The top of cover 32 also corresponds in function to the top cover 48a of FIGS. 5a-5f.

Immediately beneath the outer cover 32 is an inner cone cover 40a having a working aperture 84 and a secondary aperture 66 located about 45° from the working aperture 84. This inner cone cover 40a is rotated by the inner cone 36 and, as shown in this Fig., the inner cone 36 has a first working window 88, a secondary window 90 and a second working window 80 (outer reference window in FIGS. 5c-5f). Note also that cover 40a is identified as such since it is identical to cover 40a in FIGS. 5a-5f even though it is rotated by cone 36 which corresponds to cone 36 in FIGS. 5a-5f. In cone 36, the first working window 88 and the second working window 80 are located about 180° apart and the secondary window 90 is located about 45° from the second working window 94. This inner cone 36 also has a secondary diffuser 68 located about 180° from the secondary window 90. The outer cone 48, shown below the inner cone 36 in FIG. 7a, has the working diffuser 74 and an additional reference diffuser 92 located about 90° therefrom, the outer working window 82 located about 90° from the reference diffuser 92 and an outer reference window 94 located about 90° from the outer working window 82. The outer reference window 94 and outer working window 82 permit diffused radiation to be emitted through the field-of-view aperture 83 depending on the mode selected.

FIGS. 7a-7f show the modes of calibrating the SRCA. Since this SRCA has not only a working diffuser 74 and a secondary diffuser 68 but also an additional reference diffuser 92, more modes are needed to calibrate the three diffusers.

In these FIGS. 7a-7f, the cover 32 is shown throughout the several steps as stationary, while the inner cover 40a and the inner cone 36, while shown separately, rotate together. The outer cone 48 is shown immediately below the inner cone 36. These Figs. show the various steps by the rotation of the inner and outer cones and the location of the various apertures, windows and diffusers. These Figs. also show the directions of the solar radiance throughout the various Figs. and the instrument field-of-view aperture 83.

Mode 1 (FIG. 7a) represents the stow position. The inner cone cover 40a is located such that the working and secondary apertures 86 and 66 are within the space between the fixed secondary aperture 64 and the fixed working aperture 84 in the cover 32 so that the solar flux is blocked from reaching any diffuser or window in the cones. Similarly, the outer cone 48 is positioned such that no light can enter the instrument field of view aperture 80. Thus, the diffusers are sealed against sunlight and contamination while not in use.

Mode 2 (FIG. 7b) represents the solar calibration utilizing the working diffuser 74. This is the normal working mode of the SRCA. The inner cone 36 and its cover 40a have been rotated 90° clockwise from the stow position (Mode 1) and the outer cone 48 has been rotated 45° clockwise from the stow position. In this mode, solar flux enters the fixed working aperture 84, the working aperture 86, the first working window 88 and impinges upon the working diffuser 74 which directs its diffused radiation through the outer working window 82 and out the instrument field-of-view aperture 83 which is aligned with the outer working window 82.

Mode 3 (FIG. 7c) represents the secondary diffuser calibration. The inner cone 36 and its cover 40a have been rotated 45° clockwise from the stow position and the outer cone 48 has been rotated 45° clockwise (or remains in the same position as in Mode 2) from the stow position. In this Mode, solar flux is directed through the fixed working aperture 84, through the secondary aperture 66 and impinges upon the secondary diffuser 68 which directs its diffused radiation through the secondary window 90 and through the outer working window 82 and out the instrument field-of-view aperture 83 which are aligned.

Mode 4 (FIG. 7d) represents dual diffuser calibration for calibrating the working diffuser 74. The inner cone 36 and its cover 40a are rotated 90° counter clockwise from the stow position and the outer cone 48 has again been rotated 45° clockwise (or remains in this position from Modes 2 and 3) from the stow position. In this Mode, solar flux is directed through the fixed secondary aperture 64, through the secondary aperture 66 and impinges upon the secondary diffuser 68 which directs its diffused radiation through the second working window 80 and onto the working diffuser 74. The latter directs its diffused radiance through the outer working window 82 and through the instrument field-of-view aperture 83 with which it is aligned.

Mode 5 (FIG. 7e) is a solar calibration of the additional reference diffuser 92. The inner cone 36 and its cover 40a are rotated 90° clockwise from the stow position and the outer cone 48 is rotated 45° counter clockwise from the stow position. In this Mode, solar flux is directed through the fixed working aperture 84 and through the working aperture 86, impinging upon the reference diffuser 92 which directs its diffused radiance out the outer reference window 94 and through the field-of-view aperture 83 with which the latter is aligned.

Mode 6 (FIG. 7f) is a solar calibration of the reference diffuser 92. The inner cone 36 and its cover 40a are rotated 90° counter clockwise form the stow position and the outer cone 48 is rotated 45° counter clockwise (or remains in position as in Mode 5) from the stow position. In this Mode, solar flux is directed through the fixed secondary aperture 64, through the secondary aperture 66, to impinge upon the secondary diffuser 68 which directs its diffused radiation through the second working window 80 onto the reference diffuser 92 and out through the outer reference window 94 and the instrument field-of-view aperture 83 which is in alignment with the outer reference window 94.

THIRD EMBODIMENT

In this embodiment those components which have identical functions as in the prior embodiments will be given identical reference numerals and other components which have similar functions as in the prior embodiment will be given similar reference numerals but with the suffix a.

Figure 8:
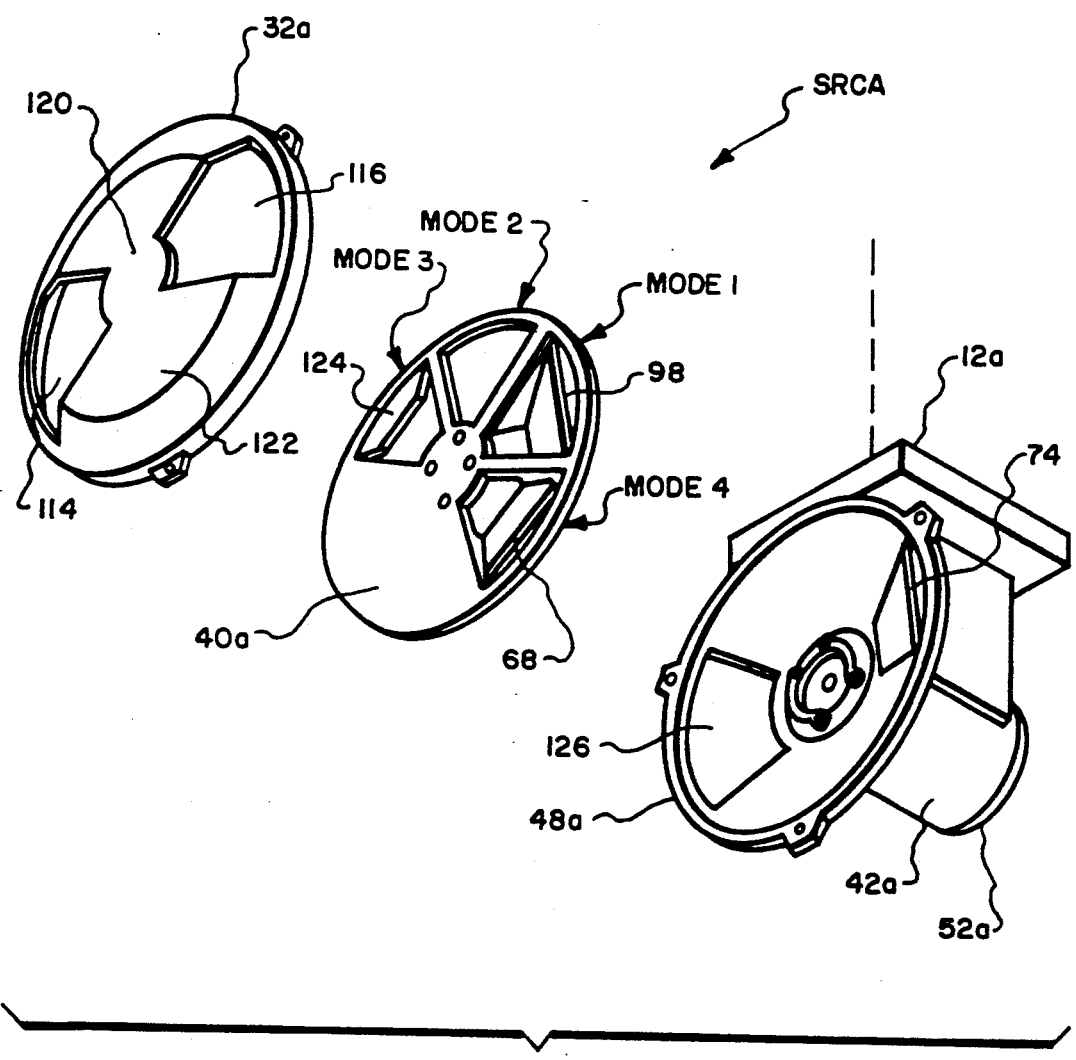
FIG. 8 is an exploded view of the third embodiment of the SRCA.
Figure 9A:
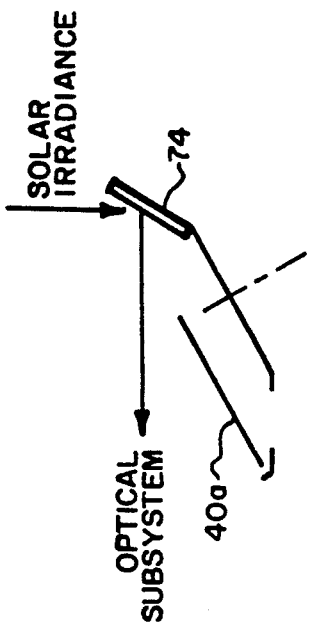
FIGS. 9a-9d illustrate the modes used in solar calibration of the SRCA of FIG. 8.
Figure 9B:
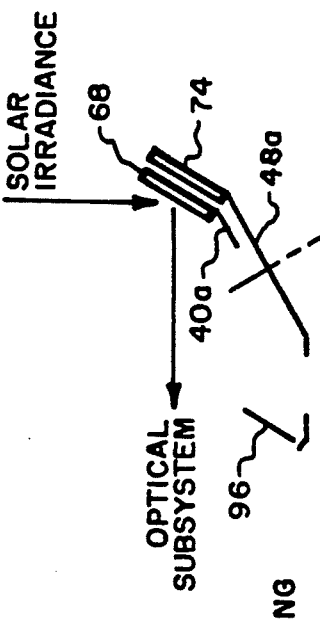
Figure 9C:
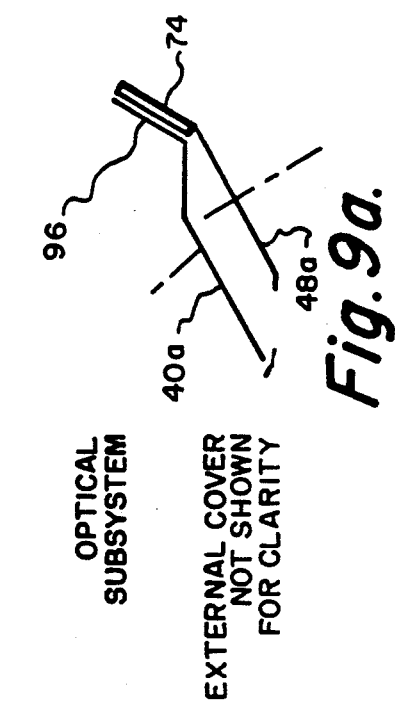
Figure 9D:
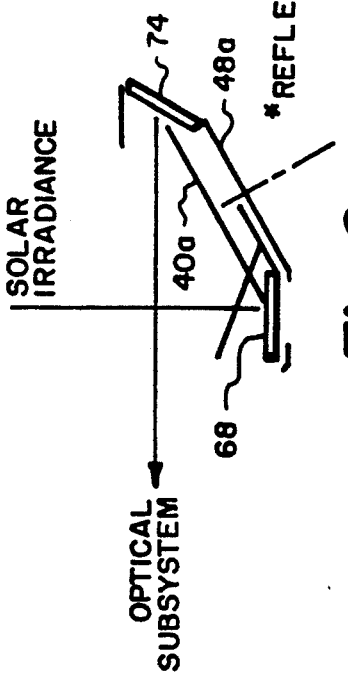

This third embodiment of the SRCA is shown in the exploded view in FIG. 8 as having an external cover 32a, a rotatable disk 40a, a cone 48a, a stepper motor 42a and one encoder 52a, all of which are connected to the TOMS by bracket 12a.

The external cover 32a is circular and has four quadrant partitions, apertures 114 and 116 in opposite quadrants and solid partitions 120 and 122 in opposite quadrants which act as covers. The external cover 32a is non-rotatably fixed to the cone 36a by any suitable means.

The rotatable disk 40a is circular and is rotatable inside the cone 36a. The disk 40a has four apertures, identified as Modes 1–4, located on two-thirds of the disk 40a with the remaining one-third being solid to act as a cover. Mode 1 aperture contains an additional diffuser 98, which may also function as a cover. Mode 2 aperture is open (or clear of any impediment), Mode 3 aperture contains an aperture block 124 and Mode 4 aperture contains a secondary diffuser 68. Mode 3 and 4 apertures are diametrically opposed to match the partitions in the external cover 32a.

The cone 48a has a fixed working diffuser 74 mounted in a fixed position diametrically opposite an aperture 126.

The disk 40a is driven by the stepper motor 42a into various positions which are verified by the encoder 52a. The disk 40a is rotated so as to move the secondary diffuser 68 relative to the working diffuser 74 for calibration measurements.

As can ben seen in FIGS. 8 and 9a–9d, the diffusers are tilted with respect to the axis of the motor 42a to perform the same function as diffusers in the prior cones.

There are four Modes of operation for this embodiment of the SRCA, each corresponding to the position of disk 40a.

The functions of the four modes are as follows:

Mode 1 (FIG. 9a): The stow position for the SRCA. In this Mode, the disk 40a is rotated to position the additional reference diffuser 96 over the working diffuser 74 to protect it from degradation. The additional reference diffuser 96, constantly exposed to space, may be used to calibrate diffuser reflectance, but if it is not needed, it could be a protective cover segment of the disk 40a.

Mode 2 (FIG. 9b): This is the normal position of the disk 40a for solar calibration. The Mode 2 aperture is positioned over the working diffuser 74 allowing the solar flux to impinge on the working diffuser 74.

Mode 3 (FIG. 9c): This is a reflectance calibration Mode. The Mode 3 aperture with its aperture block 124 blocks direct solar flux of the working diffuser 74, while the solar flux impinges on the secondary diffuser 68 to irradiate the working diffuser 74. The secondary diffuser 68 is mounted on the disk 180° opposite the Mode 3 aperture.

Mode 4 (FIG. 9d): The secondary diffuser 68 is rotated 180° from the mode 3 position so that it now covers the working diffuser 74. The solar flux illuminates the secondary diffuser 68 in this position for calibrating the secondary diffuser 68.

We claim:

1. In a space borne instrument for stratospheric measurement of ozone variations having electrical and optical subsystems and where the optical subsystem responds to solar flux and provides signals which are measured in the electrical subsystem as a means of identifying said variations, the improvement in the means of calibrating the optical subsystem by using solar flux while in space comprising, a working diffuser fixed relative to said instrument and oriented to receive the solar flux and reflect diffused flux onto the optical subsystem to provide a first signal, a reference diffuser movable relative to said instrument and to said working diffuser and oriented to one position to receive solar flux and to reflect diffused flux onto the optical subsystem to provide a second signal and to another position to receive solar flux and to reflect diffused solar flux onto the working diffuser which directs its received diffused flux onto the optical subsystem to provide a signal difference from the first and second signals as a means for calibrating the optical subsystem.

2. The improvement as claimed in claim 1 further including means for blocking solar flux from reaching the diffusers.

3. The improvement as claimed in claim 1 further including a second reference diffuser movable relative to said instrument and to the working and first reference diffuser and oriented to one position to receive solar flux and to reflect diffused solar flux onto the optical subsystem to provide a fourth signal and to still another position to receive reflected solar flux from the first reference diffuser and reflect the received reflected flux onto the optical subsystem to provide a fifth signal as a means of calibrating the optical subsystem.

4. The improvement as claimed in claim 3 further including means for blocking the solar flux from reaching all of the diffusers.

5. A method for calibrating a space borne instrument for measuring stratospheric ozone variations wherein the space borne instrument has an electrical subsystem and an optical subsystem, the steps in calibrating the optical subsystem while in space comprising, orienting a working diffuser relative to the sun to receive and diffuse solar flux and direct this diffused flux toward the optical subsystem to provide a first signal, measuring the signal generated by the optical subsystem during the first step, orienting a reference diffuser relative to the sun to receive and diffuse solar flux and direct the diffused solar flux onto said optical subsystem to provide a second signal, means measuring the signal generated by the optical subsystem during the second step, orienting a first reference diffuser relative to the sun to receive and diffuse solar flux and direct this diffused flux toward the working diffuser which directs its received diffused solar flux to the optical subsystem to provide a second signal, measuring the signal generated during this last step, comparing the signals generated during the three steps as a method of calibrating the optical subsystem.

6. The method as claimed in claim 5 including the further step of orienting a second reference diffuser relative to the sun to receive and diffuse solar flux and direct this diffused flux onto the optical subsystem to provide a fourth signal, measuring the signal generated during this fourth step, orienting said second reference diffuser to receive reflected solar flux from the first reference diffuser and reflect this reflected flux onto the optical subsystem as a method of calibrating the reference diffusers.

7. For use in a space borne vehicle for stratospheric measurement of ozone variations while in space, said vehicle having an electrical subsystem and a optical subsystem with an optical subsystem, a solar reflectance calibration assembly comprising:

a working diffuser capable of receiving solar flux while in space to reflect diffused flux into the optical subsystem, a secondary diffuser capable of receiving solar flux when in space and movable relative to said working diffuser and in one position to reflect diffused flux onto said optical subsystem and in another position onto the working diffuser which directs its received diffused flux onto the optical subsystem.

8. The assembly as claimed in claim 7 further including means for blocking solar flux from all diffusers when in space.

9. The assembly as claimed in claim 7 further including a reference diffuser capable of receiving solar flux and direct this diffused flux into the optical subsystem and capable of being moved to receive reflected solar flux from the secondary diffuser and reflect this reflected flux into the optical subsystem.

10. The improvement as claimed in claim 9 further including means for blocking the solar flux from reaching all of the diffusers.

11. In a space borne instrument for stratospheric measurement of ozone variations having electrical and optical subsystems and where the optical subsystem responds to solar flux and provides signals which are measured in the electrical subsystem as a means of identifying said variations, the improvement in the means of calibrating the optical subsystem by using solar flux while in space comprising, a fixed outer cover with first aperture means, a movable inner cone with second aperture means, a reference diffuser and a cover with third aperture means and movable with said inner cone, and an outer fixed cone with fourth aperture means and a working diffuser, said inner cone in one position allows solar flux through said first, second and third aperture means so as to impinge upon said working diffuser which reflects diffused solar flux through said third and fourth aperture means and onto said optical subsystem to provide a first signal, said inner cone in a second position allows solar flux through said first and said second aperture means so as to impinge on said reference diffuser which reflects diffused solar flux through said third and fourth aperture means and onto said optical subsystem to provide a second signal, said inner cone in a third position allows solar flux through said first and second aperture means so as to impinge on said reference diffuser which reflects diffused solar flux through said third aperture means and onto said working diffuser which reflects diffused solar flux through said third and fourth aperture means and onto said optical subsystem to provide a third signal.

12. The improvement as claimed in claim 11 wherein said inner cover in a third position blocks solar flux from reaching the diffusers.

13. In a space borne instrument for stratospheric measurement of ozone variations having electrical and optical subsystems and where the optical subsystem responds to solar flux and provides signals which are measured in the electrical subsystem as a means of identifying said variations, the improvement in the means of calibrating the optical subsystem by using solar flux while in space comprising, a first outer cover with first aperture means, a movable inner cone with second aperture means, a first reference diffuser and a cover with third aperture means and movable with said inner cone, an outer movable cone with fourth aperture means, a second reference diffuser and a working diffuser, and said inner cone in one position allows solar flux through said first, second and third aperture means so as to impinge on said working diffuser which reflects diffused solar flux through said fourth aperture means onto said optical subsystem to provide a first signal, said inner cone in a second position allows solar flux through said first and second aperture means so as to impinge on to said first reference diffuser which reflects diffused solar flux through said third and fourth aperture means and onto said optical subsystem to provide a second signal, said inner cone in a third position allows solar flux through said first and second aperture means so as to impinge on said first reference diffuser which reflects diffused solar flux through said third aperture means onto said working diffuser which reflects diffused solar flux through said fourth aperture means and onto said optical subsystem to provide a third signal, said inner cone in a fourth position allows solar flux to enter through said first, second and third aperture means to impinge upon said second reference diffuser which reflects diffused solar flux through said fourth aperture means and onto said optical subsystem to provide a fourth signal, said inner cone in a fifth position allows solar flux through said first and second aperture means so as to impinge upon said first reference diffuser which reflects diffused solar flux through said third aperture means so as to impinge upon said second reference diffuser which reflects diffused solar flux through said fourth aperture means and onto said optical subsystem to provide a fifth signal.

14. The improvement as claimed in claim 13 wherein said inner cone in still another position blocks solar flux from reaching the diffuser. flux from reaching the diffuser.

* * * * *

UNITED STATES PATENT AND TRADEMARK OFFICE
CERTIFICATE OF CORRECTION

PATENT NO. : 5,218,416
DATED : June 8, 1993
INVENTOR(S) : Robert E. Haring, et. al.

It is certified that error appears in the above-indentified patent and that said Letters Patent is hereby corrected as shown below:

Column 5, line 68, delete "4f" and insert --5f--

Column 8, line 65, delete "form" and insert --from--

Column 12, lines 66-67, delete "flux from reaching the diffuser".

Signed and Sealed this

Twenty-second Day of February, 1994

*Attest:*

BRUCE LEHMAN

*Attesting Officer*  *Commissioner of Patents and Trademarks*